(12) United States Patent
Hobbs et al.

(10) Patent No.: US 8,771,750 B2
(45) Date of Patent: Jul. 8, 2014

(54) DELIVERY OR REMOVAL OF METALS FROM BIOLOGICAL SYSTEMS

(75) Inventors: David T. Hobbs, N. Augusta, SC (US); John C. Wataha, Martinez, GA (US); Jill Lewis, Martinez, GA (US); Regina L. W. Messer, Martinez, GA (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 216 days.

(21) Appl. No.: 11/639,105

(22) Filed: Dec. 14, 2006

(65) Prior Publication Data

US 2008/0145450 A1    Jun. 19, 2008

(51) Int. Cl.
| | |
|---|---|
| A61K 33/24 | (2006.01) |
| A61K 47/02 | (2006.01) |
| A61K 31/665 | (2006.01) |
| A61K 47/48 | (2006.01) |

(52) U.S. Cl.
CPC ............... *A61K 31/665* (2013.01); *A61K 33/24* (2013.01); *A61K 47/48861* (2013.01)
USPC .............. 424/617; 424/649; 514/99; 514/769

(58) Field of Classification Search
None
See application file for complete search history.

(56) References Cited

U.S. PATENT DOCUMENTS

| | | | | |
|---|---|---|---|---|
| 4,330,530 | A * | 5/1982 | Baker | 424/649 |
| 6,268,307 | B1 | 7/2001 | DeFilippi et al. | |
| 6,517,788 | B2 | 2/2003 | Debreuille et al. | |
| 6,841,172 | B1 * | 1/2005 | Ash | 424/648 |
| 7,494,640 | B1 * | 2/2009 | Nyman et al. | 423/598 |
| 2002/0112609 | A1 * | 8/2002 | Wong | 96/131 |

OTHER PUBLICATIONS

Hobbs et al., Journal of Biomedical Materials Research Part B: Applied Biomaterials, 78B(2), pp. 296-301 (published online Dec. 16, 2005).*
Sadler et al, "Metal complexes in medicine: Design and mechanism of action", Pure & Appl. Chem., vol. 70, No. 4, pp. 863-871 (1998).*
Mirabelli et al, "Evaluation of the in Vivo Antitumor Activity and in Vitro Cytotoxic Properties of Auranofin, a Coordinated Gold Compound, in Murine Tumor Models", Cancer Res., 45, pp. 32-39 (1985).*
Hoke et al, "Mechanism of Alterations in Isolated Rat Liver Mitochondrial Function Induced by Gold Complexes of Bidentate Phosphines", J. Bio. Chem., 263(23), pp. 11204-11210 (1988).*
C.A. Nash, et al., "Engineering Monosodium Titanate for Adsorption Column Processes", WM '05 Conference, Tucson, AZ, Feb.-Mar. 3, 2005.
D.T. Hobbs, ett al., "Development of Improved Sorbents for Radiochemical Separations at the Savannah River Site"; Proceedings of the Waste Management Conference, Tuscon, AZ, Feb. 27-Mar. 3, 2005.
D.T. Hobbs, et al., "Development of an Improved Sodium Titanate for the Pretreatment of High Level Nuclear Waste at the Savannah River Site", WM '05 Conference, Tucson, AZ, Feb. 27-Mar. 3, 2005.
May Nyman and David T. Hobbs, "A Family of Peroxo-titanate Materials Tailored for Optimal Strontium and Actinide Sorption", Chemistry of Materials, published on Web, Nov. 18, 2006.
D.T. Hobbs, et al., "Adsorption of Biometals to Monosodium Titanate in Biological Environments", Savannah River National Laboratory, Westinghouse Savannah River Company and Medical College of Georgia, Journel of Biomedical Materials Research: Part B—Applied Biomaterials, vol. 78B, Issue 2, pp. 296-301, Published Online Dec. 16, 2005, Wiley Periodicals, Inc.

* cited by examiner

*Primary Examiner* — Daniel Sullivan
*Assistant Examiner* — Barbara Frazier
(74) *Attorney, Agent, or Firm* — Bennett Mullinax, LLC

(57) ABSTRACT

A process for delivering and/or removing metal from a biological system by loading a titanate sorbent with a biometal either before introduction into the system for delivery to a site within the system or after introduction into the system for delivery to a site where there is an excess accumulation of metal and thereafter the sorbent is loaded at the site with the excess metal and is removed from the system.

8 Claims, 6 Drawing Sheets

Fig. 1. Scanning electron microscope (*SEM, top*) and transmission electron microscopic (*TEM, bottom*) images of monosodium titanate (MST) particles. Bars on each micrograph indicate scale in nanometers (nm). The MST particles are roughly spherical with diameters ranging from 1-10 µm (SEM image). The particles exhibit a homogenous and amorphous inner core surrounded by an outer fringe region with a fibrous or appearance (TEM). See Reference 3 for details concerning microscopic analyses of the MST particles).

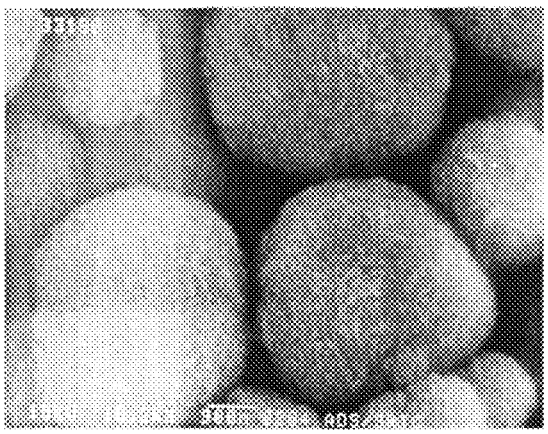

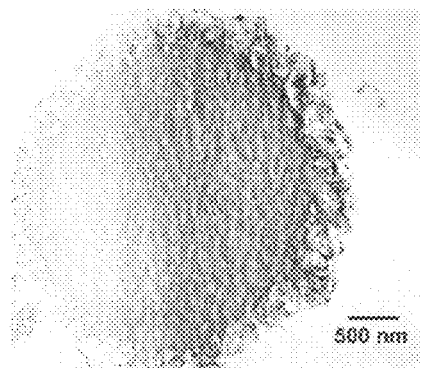

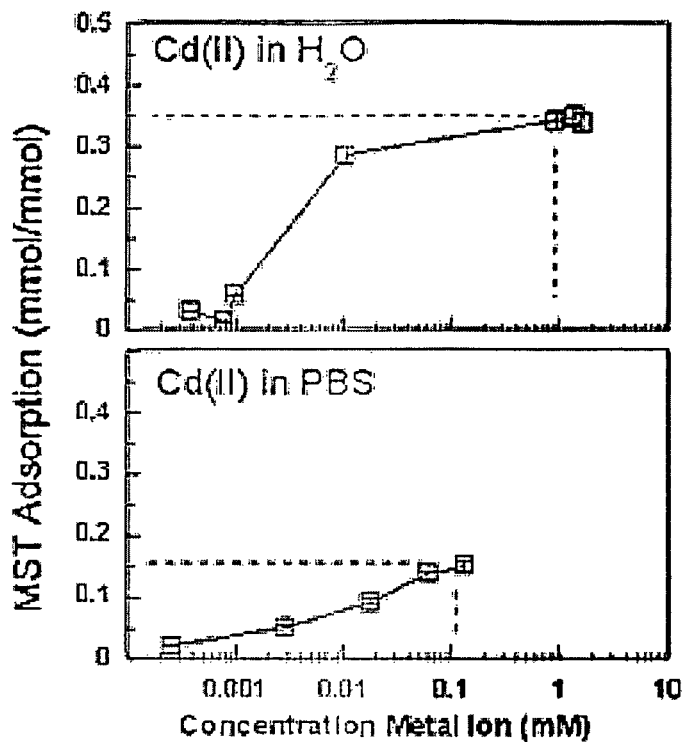

Fig. 2. Loading isotherms for Cd(II) onto monosodium titanate (MST) particles in water (top) or phosphate buffered saline (PBS, bottom) as a function of Cd(II) concentrations (mM). Adsorption was expressed as mmol of adsorbed Cd(II) per mmol of MST. Errors bars indicate errors in measurements calculated from standard error propagation formulae based on known uncertainties in the measurement of Cd(II). Dashed lines estimate MST saturation (horizontal line) and saturating concentration (vertical line).

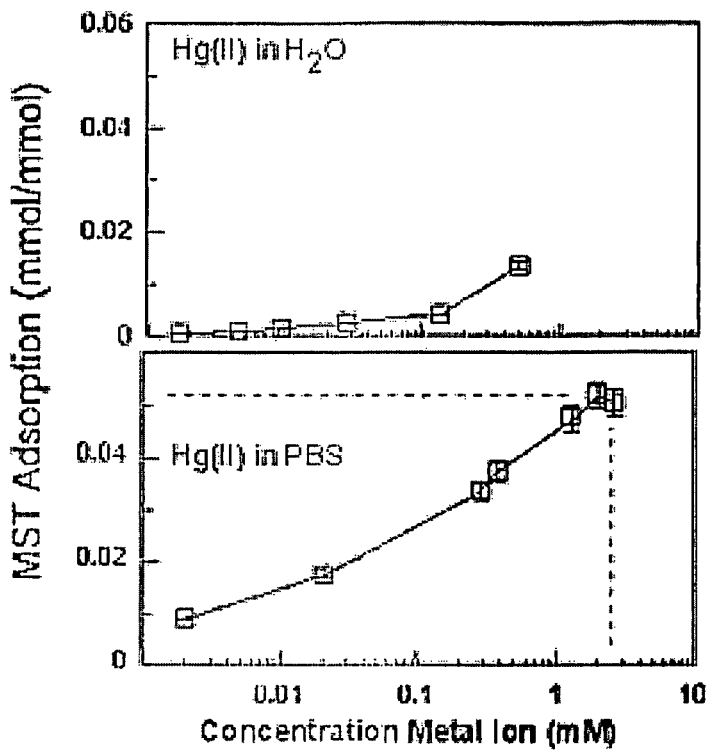

Fig. 3. Loading isotherms for Hg(II) onto monosodium titanate (MST) particles in water (top) or phosphate buffered saline (PBS, bottom) as a function of Hg(II) concentrations (mM). Adsorption was expressed as mmol of adsorbed Hg(II) per mmol of MST. Errors bars indicate errors in measurements calculated from standard error propagation formulae based on known uncertainties in the measurement of Hg(II). Dashed lines estimate MST saturation (horizontal line) and saturating concentration (vertical line). No adsorption saturation was observed in the water condition.

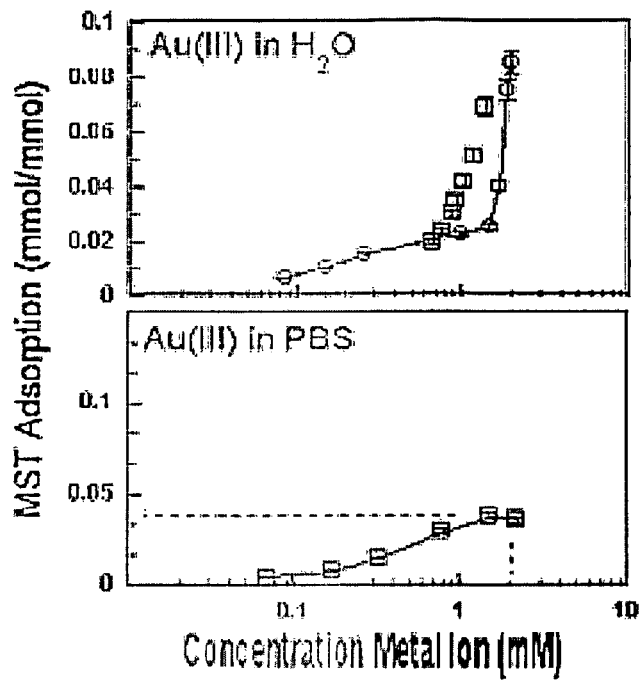

Fig. 4. Loading isotherms for Au(III) onto monosodium titanate (MST) particles in water (top, two separate experiments shown) or phosphate buffered saline (PBS, bottom) as a function of Au(III) concentrations (mM). Adsorption was expressed as mmol of adsorbed Au(III) per mmol of MST. Errors bars indicate errors in measurements calculated from standard error propagation formulae based on known uncertainties in the measurement of Au(III). Dashed lines estimate MST saturation (horizontal line) and saturating concentration (vertical line). No adsoprtion saturation was observed in the concentrations tested for the water condition.

Fig. 5. Response of human monocytic cells (THP1) to monosodium titanate (MST) particle suspensions ranging from 0.01-100 mg/L in cell-culture medium. Cellular mitochondiral response was estimated after 24, 48, or 72 h using succinate dehydrogenase (SDH) activity and the MTT assay. SDH activity was expressed as a percentage of controls without MST (dashed lines, 100%). Error bars represent one standard deviation (n = 8 per condition). Asterisks indicate differences from the controls at each concentration (2-sided t-tests, $\alpha = 0.05$).

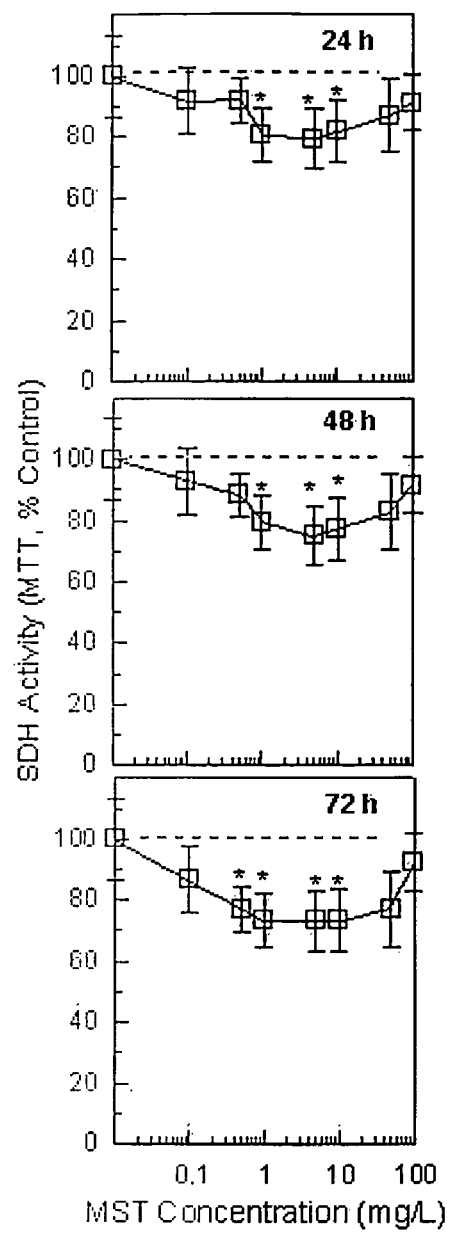

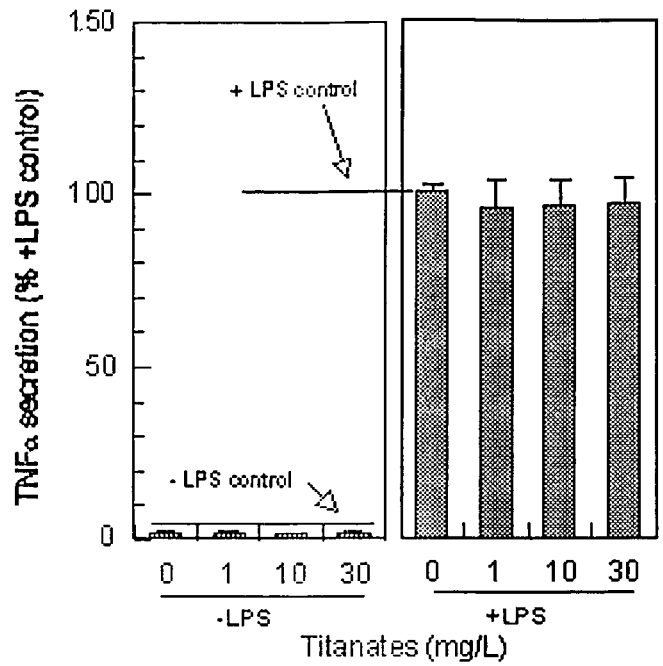

Fig. 6. Secretory response of human monocytic cells (THP1) to monosodium titanate particle suspensions ranging from 1-30 mg/L. THP1 cells were exposed to the titanates for 72 h, with or without lipopolysaccharide (LPS, 1 μg/mL) activation for the last 6 h. TNFα was measured in cell-culture medium supernatants using standard ELISA techniques. TNFα secretion was expressed as a percentage of +LPS controls (100%). Error bars (not always visible) represent standard deviations (n = 3). Within +LPS or –LPS groups, there were no statistical differences between titanate concentrations (ANOVA, Tukey post hoc, α = 0.05).

DELIVERY OR REMOVAL OF METALS FROM BIOLOGICAL SYSTEMS

FEDERALLY SPONSORED RESEARCH

The U.S. Government has rights in this invention pursuant to contract number DE-ACO9-96SR18500 between the U.S. Department of Energy and Washington Savannah River Company LLC.

FIELD OF THE INVENTION

This invention relates to the use of an inorganic material for the introduction or removal of therapeutic metals from a biological system. More particularly, the invention relates to the use of titanate sorbents, such as monosodium titanate and amorphous peroxotitanate for delivery and/or removal of biometals from biologic sites for treatment of a condition or disease.

BACKGROUND

Monosodium titanate (MST) is an inorganic sorbent that effectively removes strontium, plutonium, neptunium, and other actinide trace elements from alkaline high-level waste solutions. MST also strongly adsorbs or ion exchanges with a number of metallic species in a variety of aqueous media. As an example of some of the prior uses of MST, reference is made to U.S. Pat. No. 6,268,307 entitled "Titania Bound Sodium Titanate Ion Exchanger" which issued on Jul. 31, 2001 to DeFilippi et al. and to U.S. Pat. No. 6,517,788 entitled "Method and Device for Separating Caesium, Strontium and Transuranium Elements Contained in Sodium Waste" which issued on Feb. 11, 2003 to Debreuille et al. In addition, more recent work with MST is reported in a paper entitled "Engineering Monosodium Titanate for Adsorption Column Processes" by C. A. Nash et al. in the WM '05 Conference of Feb. 27, 2005.

MST prepared for the treatment of strongly alkaline nuclear waste solutions features a spherically-shaped particle morphology with particles ranging in diameter from about 0.5 μm to 10 μm. This material has been found to readily adsorb other metal ions such as Au (III), (Cd (II), and Hg (II) at biologically relevant pH conditions. These biologically relevant pH conditions are in contrast to conditions (pH>>12) encountered when using MST to treat nuclear waste solutions produced from reprocessing of irradiated nuclear fuel and target materials.

Recently, a related family of amorphous titanate materials referred to as amorphous peroxotitanates (APT) have been found to be even more effective than MST for the separation of strontium and actinides from waste solutions. This discovery is reported in the following papers: "Development of Improved Sorbents for Radiochemical Separations at the Savannah River Site" by Hobbs, D. T.; Nyman, M. D.; Tripathi, A.; Medvedev, D.; and Clearfield, A. in the *Proceedings of the Waste Management Conference*, Tuscon, Ariz., Feb. 27-Mar. 3, 2005; "Development of an Improved Sodium Titanate for the Pretreatment of Nuclear Waste at the Savannah River Site" by Hobbs, D. T.; Nyman, M. D.; Poirier, M. R.; Barnes, M. J.; Stallings, M. E. in the *Proceedings of the Symposium on Waste Management*, Tuscon, Ariz., Feb. 26-Mar. 2, 2006; and, "A Family of Peroxotitanate Materials Tailored for Optimal Strontium and Actinide Sorption," by Nyman, M. D.; Hobbs, D. T. in the *Chemistry of Materials*, published on Web Nov. 18, 2006.

While the prior art use of sodium titanates as mentioned above has focused generally on the separation of radionuclides in spent nuclear fuel, the affinity of the sodium titanates to adsorb or ion exchange with other metals has not been significantly investigated or developed. Accordingly, it is one object of the present invention to develop unique and novel processes and products that advantageously use the metal binding properties of sodium titanates at physiologically acceptable pH levels.

A number of metals are used as therapeutic agents in the treatment of diseases. These metals are often introduced as metal complexes in which metal ions are attached to organic ligands. The organic ligands are utilized to increase the solubility of the metals at physiological pH levels (ca. 7.3) which facilitates transport in the blood system for delivery of the metal to the affected organ. These ligands also reduce the systemic toxicity of the uncompleted metal ions. Often, large quantities of the metal complexes are injected systemically to provide sufficient amounts of metal for the desired therapeutic effect at a specific site. Systemic administration can be problematic and result in toxic reactions if metal ions accumulate and undesirable metal ion concentrations occur. Accumulated metal ions can prove difficult to remove from the affected organ or site due to low solubility at the physiological pH level and formation of complexes in tissues.

Accordingly, it is the object of the present invention to provide a novel method for metal ion delivery or removal using an inert inorganic substance such as monosodium titanate (MST) or amorphous peroxotitanates (APT) that are effective at the physiological pH levels. Novel uses of MST and APT are described below.

SUMMARY OF THE INVENTION

As used herein, the term "titanate sorbent" will be understood to include sodium titanate, monosodium titanate (MST) and amorphous peroxotitanate (APT). MST is a white, inorganic, amorphous, poorly crystalline sodium titanate sorbent material that exhibits high affinity for strontium and actinide radioisotope at strong alkaline, sodium containing solution but has affinity for the therapeutic or biometal in near neutral solution. MST's chemical formula is

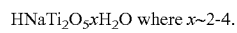
HNaTi$_2$O$_5$·xH$_2$O where x~2-4.

APT is also amorphous and poorly defined but has similar if not stronger affinity for the biometals than MST. Its general formula is:

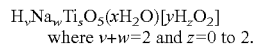
H$_v$Na$_w$Ti$_x$O$_5$(xH$_2$O)[yH$_2$O$_2$]
where v+w=2 and z=0 to 2.

In one aspect the subject invention is the process of delivering and/or removing metals in biological systems. Preferably, the biological system is the human body but it may also be any plant or animal system. The APT or the MST may be used alone or may be used together in any proportion depending on the metal and sites involved. The selection of which titanate sorbent or combination thereof can be readily determined by those skilled in the art.

In another aspect, this invention is a method for in vivo delivery of metals to selected sites for therapeutic purposes by loading the desired therapeutic metal onto a titanate sorbent compound and delivering the loaded sorbent to the site.

In yet another aspect, a metal-loaded sorbent is prepared in a buffered solution having a pH level in the range of about 7.0 to about 7.5, and the solution with the loaded sorbent is introduced into a physiological system of a patient so that the metal will be conveyed to the selected site where loaded sorbent accumulates or the metal is released to accumulate. The selected site may be an organ, bone joint, or other treatable site.

In another aspect, the present invention includes the step of introducing the titanate sorbent loaded with a selected biometal into the patient by injecting it into tissue which is the target for treatment.

In an alternate embodiment, the solution containing titanate sorbent loaded with a therapeutic metal may be orally ingested by the patient to treat conditions of the digestive tract. Alternatively, unloaded titanate sorbent may be orally ingested to remove unwanted metals from the digestive tract.

In yet another aspect, a biometal or treating metal compound such as auranofin is loaded onto the sorbent titanate, the loaded sorbent is compacted into a tablet, pellet, or wafer, and then is implanted into a site such as a tumor.

The invention may be better understood by reference to the detailed description which follows.

DETAILED DESCRIPTION

Metals or metal compounds having known therapeutic value include but are not limited to gold, (e.g., Au(I), as present in auranofin), Pt, Pd, Cu and Fe. In addition, radioisotopes of these or other metals that emit a desired type of radiation for therapy or imaging may be employed. Biological system includes any in vivo, ex vivo, or in vitro tissue, organ or organism, including the nutrient delivery system of plants.

For example, titanates loaded with gold may be used to treat rheumatoid arthritis in the joints of the body. Radioisotopes that can be loaded are for example, Sr-90 (beta-emitter) and a number of others specifically tailored to provide the desired type and energy of radiation (e.g., beta, gamma and/or alpha).

In a best mode and preferred embodiment, titanate sorbent is loaded with gold by the following process: Auranofin (10.3 mg) in 1 mL of absolute ethanol is dissolved in 50 mL of a phosphate buffered saline solution to provide a gold concentration of 0.304 mM. Twenty (20) mL of the gold solution and 0.25 grams of MST or APT are placed in a plastic centrifuge tube and tumbled for 10 days at ambient laboratory temperature. The centrifuge tube is then removed from the tumbler and placed in a centrifuge and spun for 5 minutes at 4000 rpm. The clear, colorless liquid is pipetted off of the solid plug. The solids are rinsed with 1.0-mL of a phosphate saline solution (without auranofin), centrifuged as before and the rinse solution is pipetted off of the solids. The rinsing of the solids is repeated and the solids stored as a moist powder. The foregoing process may be generally used with appropriate modification for other metals or metal compounds.

An appropriate quantity of the loaded titanate sorbent and volume of saline solution is selected for the treatment strategy. The concentration of metal to be loaded onto the sorbent can be determined directly by analyzing the solids for metal content or indirectly by measuring the metal concentration in the PBS solution before and after contact with the sorbent. The metal-loaded sorbent is combined with the sterile saline solution and mixed to provide a homogeneous suspension.

The suspension of unloaded titanate sorbent in a saline solution is prepared as described above using MST that has not been contacted with the metal-containing phosphate buffered saline solution.

Dialysis may be employed to remove unwanted metal by passing the patient's blood through unloaded titanate fixed to a column or other membrane to affect removal of the excess metal from the blood.

Upon reading the foregoing disclosure, variations and other embodiments of the invention may become apparent to those skilled in the art. However, the invention is to be limited only by the scope of the claims which follow below.

We claim:

1. A method for delivering selected metals or metal compounds having therapeutic treatment properties to a selected site in the biological systems of human and animal patients comprising the steps of:
   a) selecting a biometal from the group consisting of metals and metal compounds known to have a beneficial effect for a patient when delivered to the selected site;
   b) loading a titanate sorbent with said biometal; and
   c) delivering the loaded sorbent to the selected site within said biological system whereby a portion of said loaded sorbent is absorbed at the site; and,
   (d) removing excess loaded sorbent from said system.

2. The method of claim 1 wherein the site is selected from the group consisting of bone, joints, and tumors in a human body.

3. The method of claim 1 wherein the biological system is selected from the group consisting of an organ, the digestive system, urinary system, lymph, blood and respiratory system of a human body.

4. A method for delivery of metals or metal compounds having therapeutic treatment properties to selected sites in a biological system of a human or animal patient where a health problem exists that is expected to beneficially respond to the deliver of said metals, said method comprising the steps of:
   a) loading a selected therapeutic metal or metal compound onto a titanate sorbent selected from the group consisting of MST having a general chemical formula of $HNA Ti_2O_5xH_2O$ where $x\sim2\text{-}4$ and APT having a general chemical formula of $H_vNa_wTi_sO_5(xH_2O)[yH_zO_2]$ where $v+w=2$ and $z=O$ to 2;
   b) delivering the titanate sorbent to the selected site of a patient whereby the metal that accumulates at the site provides a therapeutic treatment; and
   c) removing the loaded sorbent from the system.

5. The method of claim 4 wherein step b) is performed by oral ingestion by the patient.

6. The method of claim 4 wherein step b) is performed by injection into the tissue of the selected site.

7. The method of claim 4 wherein the therapeutic metal includes gold, said gold being the organogold compound auranofin based on Au(I) and the loading step is performed by the steps of dissolving auranofin in ethanol in a phosphate buffered saline solution with MST or APT, tumbling the solution in a centrifuge tube, and centrifuging the suspension to produce separable layers of the solution with loaded MST or APT depleted in the therapeutic metal and the MST and APT solids loaded within the therapeutic metal.

8. The method of claim 4 wherein:
   i) the titanate sorbent is loaded with a metal selected from the group consisting of gold, platinum and compounds thereof;
   ii) said loaded sorbent is delivered to the biological system of a patient selected from the group consisting of human and animal patients;
   iii) the titanate sorbent is amorphous peroxotitanate (APT);
   iv) the selected site is the site of a tumor; and
   v) the method of delivery is by injection.

* * * * *